(12) United States Patent
Tsai et al.

(10) Patent No.: US 6,286,613 B1
(45) Date of Patent: Sep. 11, 2001

(54) IMPACT METHOD AND THE DEVICE USED IN STANDARD PENETRATION TEST

(75) Inventors: Jiin-Song Tsai, 12th Fl., No. 288, Tung-An Rd., East Dist., Tainan City (TW); Chin-Chih Chen, Kaohsiung (TW); Lee-Der Jou, Kaohsiung Hsien (TW); Ke-Lon Chen, Kaohsiung (TW)

(73) Assignee: Jiin-Song Tsai, Tainan (TW)

( * ) Notice: Subject to any disclaimer, the term of this patent is extended or adjusted under 35 U.S.C. 154(b) by 0 days.

(21) Appl. No.: 09/481,835

(22) Filed: Jan. 12, 2000

(51) Int. Cl.7 ............................................. G01N 3/00
(52) U.S. Cl. ............... 175/20; 175/27; 175/50; 175/51; 175/135; 73/84
(58) Field of Search .................. 175/19, 20, 24, 175/27, 40, 50, 51, 58, 135, 162, 170, 189, 202, 203, 244, 253; 73/81, 82, 84, 85

(56) References Cited

U.S. PATENT DOCUMENTS

| | | | |
|---|---|---|---|
| 3,934,656 | * | 1/1976 | Pappert . |
| 4,405,020 | * | 9/1983 | Rassieur . |
| 4,594,885 | * | 6/1986 | Rodger . |
| 4,977,965 | * | 12/1990 | Rupe . |
| 4,993,500 | * | 2/1991 | Greene et al. . |

* cited by examiner

Primary Examiner—Roger Schoeppel
(74) Attorney, Agent, or Firm—Stoel Rives LLP

(57) ABSTRACT

A point-contact impact method used in the Standard Penetration Test (SPT) is disclosed. The method aims firstly to have the impact between the drop hammer and the anvil in the form of point contact and secondly to center the impact contact on the anvil face, such that the efficiency and the consistency of the energy transmission in the SPT greatly increase. With such a method, the ground condition of a specific site investigated by the SPT is able to be better determined. A device of the present method used in the Standard Penetration Test is a specially shaped anvil mounted on top of a rod, and the drop hammer is movably in contact with the anvil. The contact area of the anvil struck by the hammer is then limited and concentrated at the center. The impact between the hammer and the anvil is thus focused at or very near the center of the anvil, which reduces the energy loss during energy transfer from the hammer to the anvil.

13 Claims, 18 Drawing Sheets

Dimension of hammers, anvil and rod

|  | Diameter (mm) | Length (mm) | Weight (kg) | Remark |
|---|---|---|---|---|
| Hammer A | 98 | 1080 | 63.5 | |
| Hammer B | 139 | 540 | 63.5 | |
| Hammer C | 196 | 270 | 63.5 | |
| Safety hammer | 137/100* | 1084 | 63.5 | |
| Round top anvil | 80 | 120 | 4.3 | |
| Flat top anvil | 80 | 120 | 4.5 | |
| Rod | 41.2/28.5* | 3000 | 16.5 | A-sized |

* outer diameter/inner diameter

FIG.3

| Hammer | No. of Test | Results of flat top anvil | | Results of round top anvil | |
|---|---|---|---|---|---|
| | | $ER_r$ (%)[a] | $ER_i$ (%)[b] | $ER_r$ (%)[a] | $ER_i$ (%)[b] |
| Hammer A | 1 | 50.48 | 85.91 | 58.77 | 99.97 |
| | 2 | 46.47 | 79.50 | 58.79 | 100.00 |
| | 3 | 57.53 | 97.90 | 59.05 | 100.44 |
| | 4 | 44.46 | 75.65 | 59.48 | 101.16 |
| | 5 | 49.18 | 83.69 | 59.17 | 100.65 |
| | 6 | 42.32 | 72.02 | 58.77 | 99.97 |
| | 7 | 55.81 | 94.98 | 58.25 | 99.08 |
| | 8 | 59.96 | 102.04 | 59.03 | 100.41 |
| | 9 | 57.11 | 97.18 | 59.21 | 100.72 |
| | Avg. | 51.51 | 87.65 | 58.95 | 100.27 |

FIG.4a

|  |  |  |  |  |  |
|---|---|---|---|---|---|
| Hammer B | 1 | 54.52 | 92.78 | 57.73 | 98.24 |
|  | 2 | 55.77 | 94.90 | 59.09 | 100.55 |
|  | 3 | 54.41 | 92.59 | 58.59 | 99.70 |
|  | 4 | 52.51 | 89.36 | 59.51 | 101.27 |
|  | 5 | 47.78 | 81.31 | 58.66 | 99.81 |
|  | 6 | 50.60 | 86.10 | 59.41 | 101.10 |
|  | 7 | 51.11 | 86.97 | 58.55 | 99.63 |
|  | 8 | 55.58 | 94.58 | 58.78 | 100.02 |
|  | 9 | 52.73 | 89.73 | 59.56 | 101.34 |
|  | Avg. | 52.78 | 89.81 | 58.76 | 100.19 |
| Hammer C | 1 | 54.87 | 93.37 | 57.77 | 98.31 |
|  | 2 | 50.01 | 85.10 | 57.79 | 98.34 |
|  | 3 | 46.88 | 79.77 | 58.05 | 98.78 |
|  | 4 | 52.57 | 89.46 | 59.48 | 101.22 |
|  | 5 | 51.09 | 86.94 | 57.18 | 97.30 |
|  | 6 | 48.20 | 82.02 | 56.77 | 96.60 |
|  | 7 | 52.52 | 89.37 | 57.25 | 97.42 |
|  | 8 | ------ | ------ | 59.03 | 100.45 |
|  | 9 | ------ | ------ | 58.21 | 99.05 |
|  | Avg. | 50.88 | 86.58 | 57.95 | 98.61 |

FIG.4b

| | | | | | |
|---|---|---|---|---|---|
| Safety | 1 | 52.80 | 89.85 | 57.08 | 97.13 |
| | 2 | 51.22 | 87.16 | 57.96 | 98.63 |
| | 3 | 58.26 | 99.14 | 59.73 | 101.64 |
| | 4 | 50.70 | 86.28 | 59.39 | 101.06 |
| | 5 | 53.00 | 90.19 | 59.12 | 100.60 |
| | 6 | 48.03 | 81.73 | 58.85 | 100.14 |
| | 7 | 51.91 | 88.33 | 58.40 | 99.38 |
| | 8 | 49.56 | 84.34 | 56.85 | 96.74 |
| | 9 | 59.35 | 100.99 | 58.15 | 98.95 |
| | Avg. | 52.76 | 89.78 | 58.39 | 99.36 |

(a) $ER_f$: Energy ratio determined by direct integration of the measured force-time history.

(b) $ER_i$: Corrected energy ratio according to the correction specified in ASTM 4633-86.

FIG.4c

Anvil with plain face

Anvil with curved face

Wave form in the impact duration

Wave form in the impact duration

Wave form in the impact duration

Wave form in the impact duration

Wave form in the impact duration

Wave form in the impact duration

Wave form in the impact duration

Wave form in the impact duration

IMPACT METHOD AND THE DEVICE USED IN STANDARD PENETRATION TEST

BACKGROUND OF THE INVENTION

1. Field of Invention

The present invention relates to an impact method and a device used in the Standard Penetration Test (SPT). The purpose of the point-contact impact method is to improve the impact efficiency of the SPT, while the purpose of a specially shaped anvil is to generate a point-contact impact condition. The present invention is able to improve not only the impact efficiency but also the accuracy of the SPT results.

2. Description of Related Art

Geotechnical engineers in the United States commonly use the Standard Penetration Test (SPT) in subsurface investigations for routine foundation design.

As a common practice, the routine foundation design is accomplished using the SPT results (the N-value). Almost all site investigations in some areas of the United States involve the use of the SPT. There is an American Society for Testing and Materials (ASTM) Standard Method (D1586-99) for performing the SPT entitled, "Standard Test Method for Penetration Test and Split-Barrel Sampling of Soils". The ASTM Standard Method probably defines the SPT test for most engineering users.

The Standard Penetration Test (SPT) consists of driving a split-barrel sampling "spoon" or sampler a distance of 30 cm (12 in) after first "seating" the sampler 15 cm (6 in) by dropping a 63.5 kg (140 lb) hammer from a height of 76 cm (30 in). In field practice, the sampler is driven to a designated depth through a borehole using a long rod, and the hammer strikes the top end of the rod above the ground surface. The operator counts the number of blows that it takes to advance the sampler each of three 15 cm (6 in) increments. When the sampler has penetrated 45 cm (18 in) into the soil at the bottom of the borehole, the operator adds the number of blows for the second and third increments. This combined number is the result of the SPT and is called the "blow count" and is customarily designated as "N" or the "N value". It directly reflects the penetration resistance of the ground or the soil under investigation.

The SPT is used as the primary soil descriptor in a geotechnical engineering (or foundation engineering) analysis and design. In most practices, the SPT is used in conjunction with other laboratory and field testing procedures and serves as an indicator of the soil profile. The SPT has been correlated with the soil's capacity to resist ground failure or excessive settlement once a new building is put on. Therefore, the N-values obtained on a specific site are very important criteria for engineers to evaluate the stability and the possible settlement of new building to be constructed. From a logical perspective, engineers have a basic understanding that a dense soil or solid ground should have a higher N value because of a higher penetration resistance. Previous experience has correlated the ground conditions of some soil types, such as sand and clay, to certain N values. The following table shows a typical correlation of the N value ranges and the corresponding ground condition.

| SAND | | CLAY | |
|---|---|---|---|
| N Value | Ground Condition | N Value | Ground Conditions |
| — | — | 0–2 | Extremely Soft |
| 0–4 | Extremely Loose | 2–4 | Soft |
| 4–10 | Loose | 4–8 | Firm |
| 10–30 | Medium Dense | 8–15 | Stiff |
| 30–50 | Dense | 15–30 | Very Stiff |
| >50 | Very Dense | >30 | Hard |

Previous studies have shown that the N value is closely related to the energy delivered to the rod by the hammer impact. In consequence, any significant variation in the energy transmitted to the rod from the hammer can result in a dramatic effect on the N value. For example, when the pounding effect or the energy transfer between the hammer and the rod is poor and the energy delivered to the rod is lower than what is expected, the resulting N value will be higher than it should be. This will seriously bias the engineer's judgement and lead to a faulty conclusion with regard to the subsequent design and construction. Due to the described shortcoming, an improved method with a specific device is thus proposed here to provide an effective impact technique to transmit consistent energy.

With the reference to FIG. 8, the conventional equipment used to perform the SPT consists of a rod (80), an anvil (82) securely mounted on the top of the rod (80), a sampler (85) attached to the bottom of the rod and a drop hammer (86). To carry out the SPT, the hammer (86) is lifted to a height of 30 in (76 cm) above the anvil (82) and the hammer (86) is supposed to "free-fall" drop to impact the anvil (82). The induced impact energy will then transmit through the rod (80) and down to the sampler (85). In this procedure, the stress wave of the impact can be measured by a sensor (83) attached to the rod with the signal received by the sensor transmitted to a computer (84) near by. The transferred impact energy is then calculated by the computer.

In the current practices, there is no specification for the shape and method of lifting and dropping the hammer (86). Various types and shapes of hammer are used, and many different methods of lifting and dropping the hammer are employed now. In the most recent ASTM D1586-99 standard, the only requirement for the hammer (86) is that it has a weight of 140 lb (about 63.5 kg), while the requirements for the lift-drop method only require that the hammer (86) be dropped in a free-fall condition at a height of 30 in (76 cm) from the anvil (82). As a result, significant variation in the energy transferred to the rod by the hammer impact often occurs simply because of improper operation in performing the test and, especially, some inherent mechanical problems. According to previous experience and the test results, approximately 40–90% of the ideal impact energy (475 joules) can be lost before and during the hammer impact due to various factors. In order to overcome the defects, some procedural and equipment improvements have been proposed. For example, a so call "safety hammer" is widely used in current practice. The safety type hammer is designed as a steel tube, which encloses the rod (80) and the anvil (82). Most of the weight of the hammer is contributed to the attached top cover of the tube, and the hammer impacts the anvil inside the tube. This hammer has improved the safety to workers during the SPT. The method of inside hammer impact also improves the accuracy of the hammer strike. Nevertheless, this method still leaves the energy transfer problems unsolved. Previous research has concluded that there are two main difficulties that effect the energy transfer and the energy transfer stability during the SPT:
(1) Mechanical friction during the test is inevitable in most mechanical designs.
(2) Inconsistent contact between the hammer and the anvil at impact.

In fact, the friction problem can be reduced to a very insignificant level if a good mechanical design together with proper operation can generate a nearly ideal free-fall of the hammer. The most difficult problem to overcome in the current practice is to effectively deal with the inconsistent contact problem. With reference to FIG. 9, the impact contact between the hammer and the anvil is suppose to be uniformly distributed on the entire anvil top, and the resultant impact force applied to the center of the anvil. Nevertheless, non-uniform contact is not uncommon in real practice, since the hammer is very likely to drop eccentrically due to imperfect mechanical control, i.e. the alignment of the hammer and the anvil and rod are not coincident. Accordingly, the resultant impact force and thus the energy transfer from the hammer to the anvil and rod are seriously affected. The efficiency and the inconsistency of energy transfer by the hammer impact may cause the results to differ greatly from SPT predictions. Hence, the present invention intends to provide an improved method and devices to mitigate and obviate the aforementioned problem.

SUMMARY OF THE INVENTION

The main objective of the invention is to provide a new impact method used in the Standard Penetration Test (SPT) to improve the impact efficiency and the energy transfer consistency. This method proposes a point contact procedure to replace the planar contact procedure of the conventional SPT. Therefore, the impact surface between the hammer and the anvil changes from a face to face (i.e., plane to plane) condition to a face to point condition. With the change, the resultant impact force can much more easily strike at the center point of the anvil and thus along the axial of the rod. In the mean time, a true free-fall procedure is adopted to drop the hammer during the SPT, such that no energy loss due to mechanical friction needs to be considered.

The proposed point-contact impact can be accomplished by using a specially shaped anvil. Possible alternatives at least include a round top anvil, a flat top anvil with a bump at the center of the top face, and a curved top anvil with or without a bump at the center of the top face. In the mean time, the hammer face can be flatted, round or curved.

Other objects, advantages and novel features of the invention will be more apparent from the following detailed description when taken in conjunction with the accompanying figures.

BRIEF DESCRIPTION OF THE FIGURES

FIG. 3 is a table of the dimensions of the chosen hammer types and the anvils used in the experiment in accordance with the present invention;

FIGS. 4(*a*), (*b*) and (*c*) are tables of the test results of the experiments in accordance with the present invention;

DETAILED DESCRIPTION OF THE PREFERRED EMBODIMENT

Figure 1:
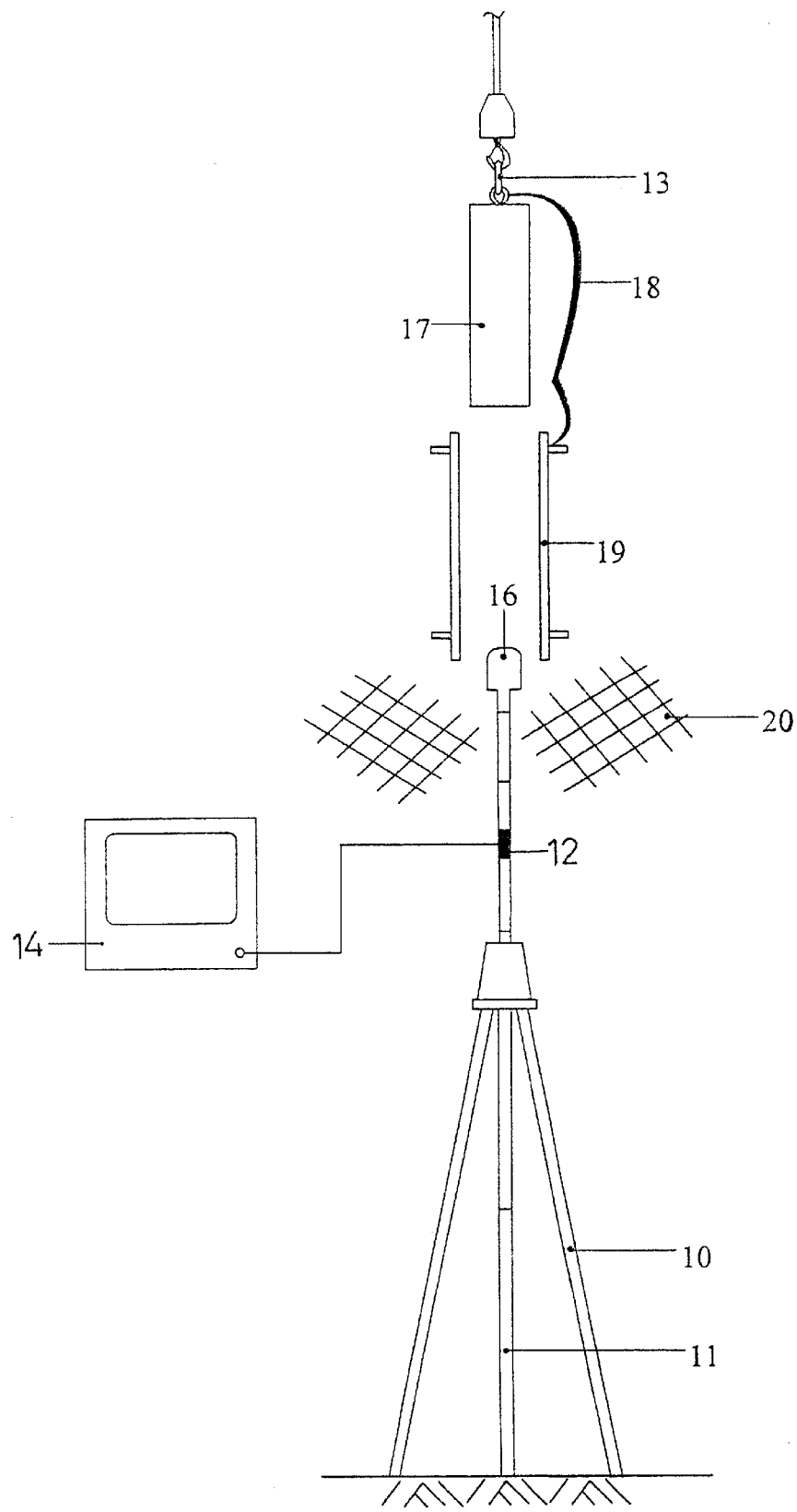
FIG. 1 is the side view of the experimental setup with a round-top anvil in accordance with the present invention.

To verify the benefit of the present invention, experiments have been conducted. With reference of FIG. 1, the experimental setup with the device in accordance with the present invention consists of three main components: a hammer (17), a rod (11) with a specially shaped round-top anvil (16) and installed sensor instrumentation (12). A lift crane and auxiliary devices, including a tripod guide (10), a safety cable (18), a hoop hammer-guide (19) and a scaffold with safety net (20), are also equipped. The round top anvil is one of the alternatives that can be adopted to generate the point-contact impact specified in the present invention. Other alternatives include but are not limited to a curved top anvil, a flat top anvil with a bump at the center of the top face and a curved top anvil with a bump at the center of the top face. Also, besides the flat face hammer used in the experiments, the hammer face can be curved or rounded. The crane lifts the hammer using a wire strap (13), and the hammer is released at a height 76 cm above the anvil by cutting the strap (13) to create a true free fall condition. The tripod guide (10) holds the rod (11) in a vertical position. Frictionless bearings in the guide (10) provide lateral support to the rod (11), while the movement of the rod (11) in vertical direction remains unrestrained. The sensor (12) installed in the rod (11) senses and transmits the transmitting force-time history in the rod (11). During the hammer (17) impact, the data measured by the sensor (12) are immediately transferred to a computer (14) nearby.

Figure 2:
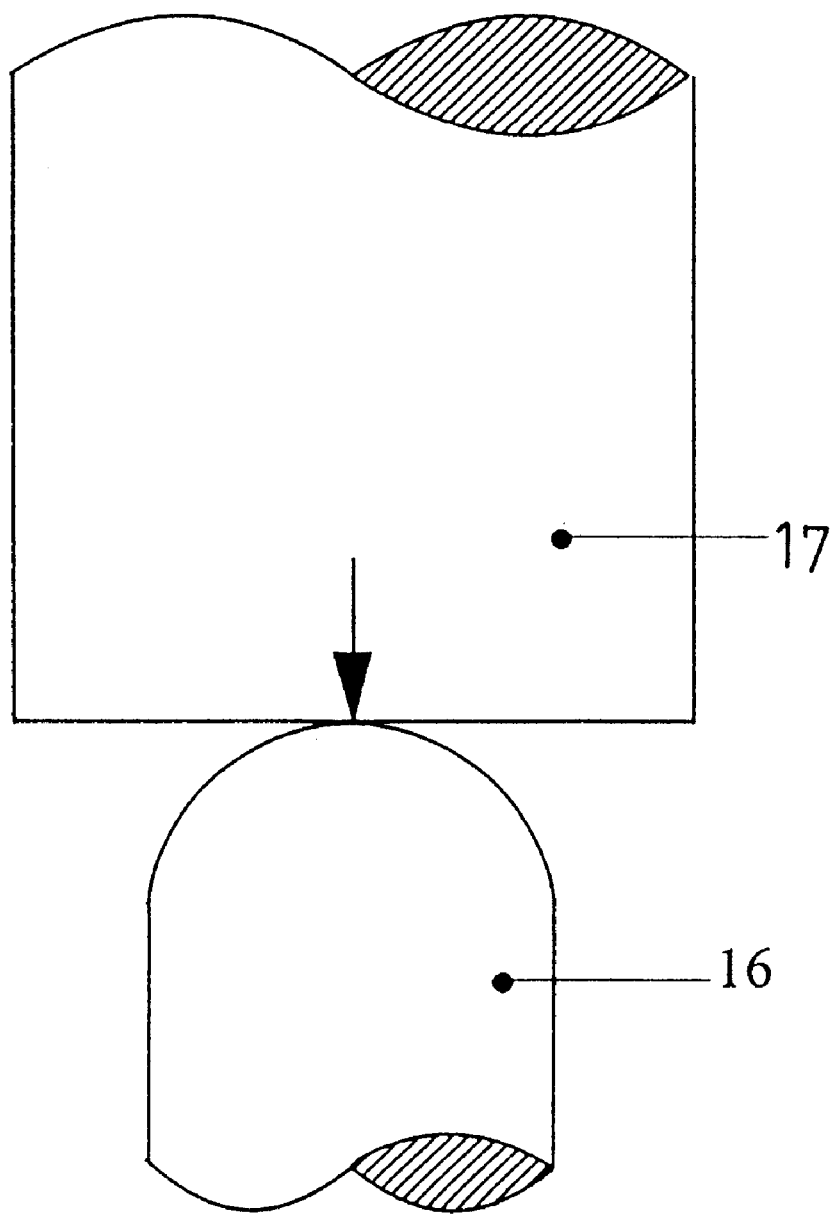
FIG. 2 is the side view of an example of a point contact between the flat end hammer and round top anvil in FIG. 1.
Figure 9:
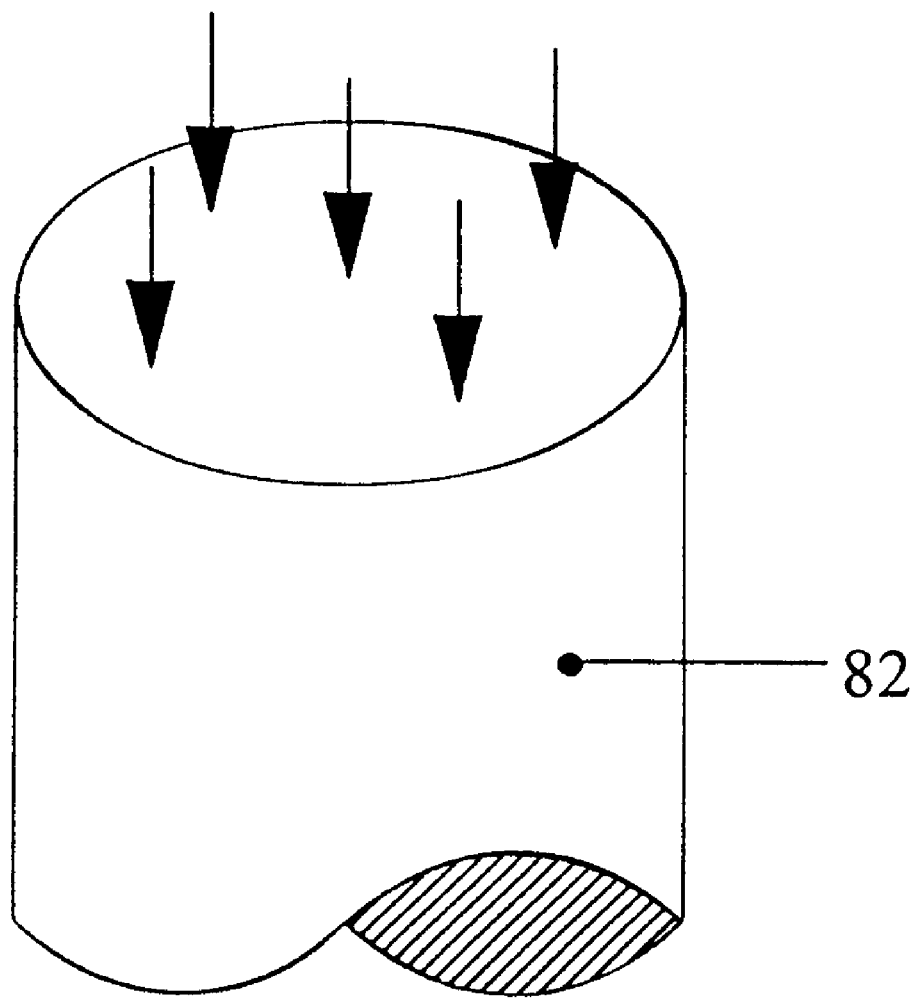
FIG. 9 is the conventional SPT impact contact between a flat end hammer and a flat top anvil.

As shown in FIG. 2, the anvil (16) used in the experiments has a round top face, such that, the contact point between the hammer (17) and the anvil (16) can be limited to the center or to a very small area around the center of the anvil. This improves the randomly distributed hammer-anvil contact of the SPT when a flat top anvil is used (FIG. 9). Other shapes of ensuring the impact between the hammer and the anvil to be a point contact can also be used, such as, for example, the anvil has a rounded top face and the hammer has a flat face, the anvil has a flat top face with a bump at the center of the anvil face and the hammer has a flat face, the anvil has a curved top face with a bump at the center of the anvil face and the hammer has a flat face and the anvil has a curved top face and the hammer has a curved face. The induced efficiency and consistency of the energy transfer of the SPT are thus better. Also, a true free-fall procedure is employed to drop the hammer with no mechanical friction so that no energy loss is involved before the impact.

Figure 5A:
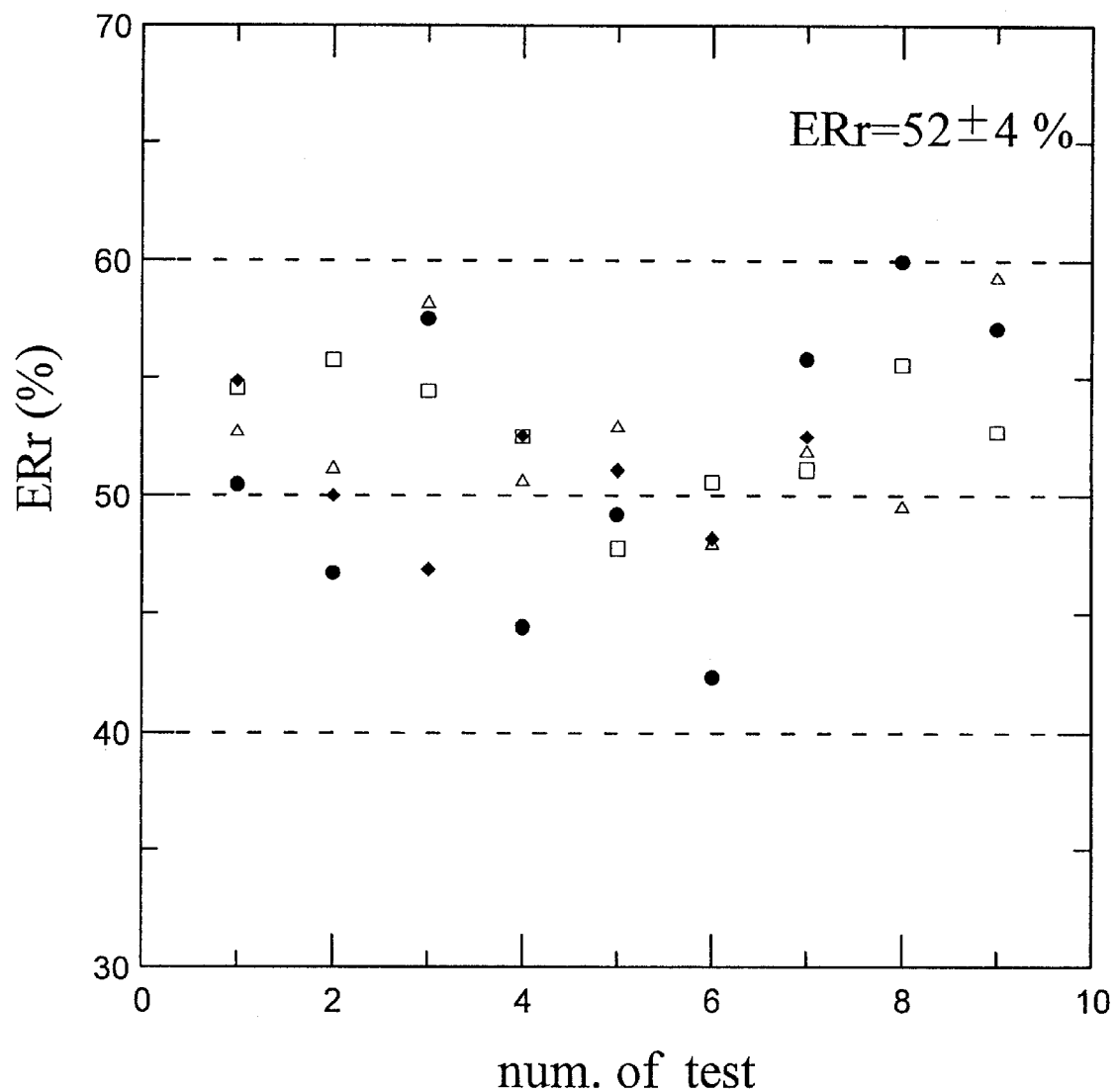
FIG. 5 is a comparison of the energy transfer ratios in the experiments when using a flat top anvil and a round top anvil.
Figure 5B:
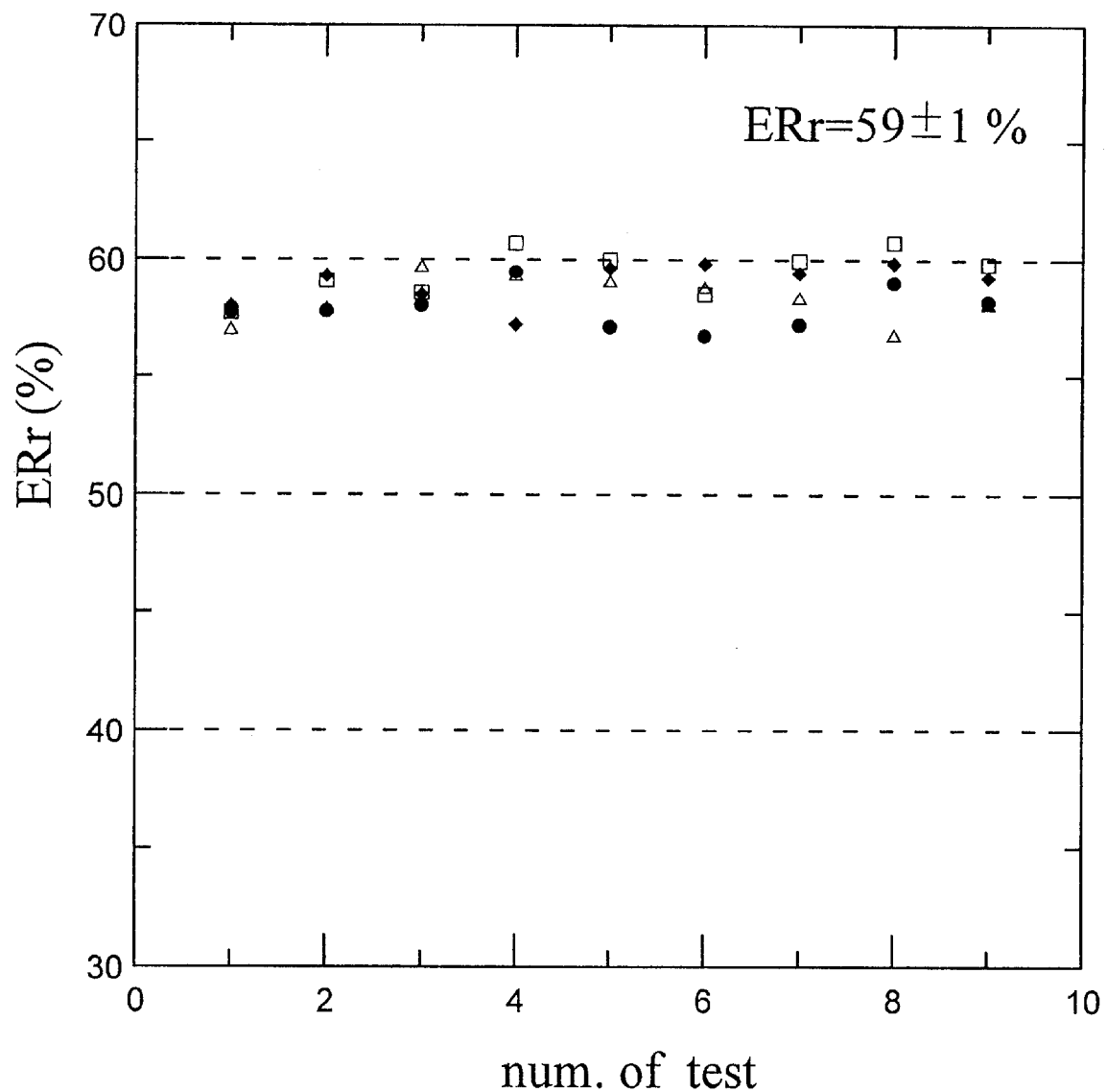
Figure 6A:
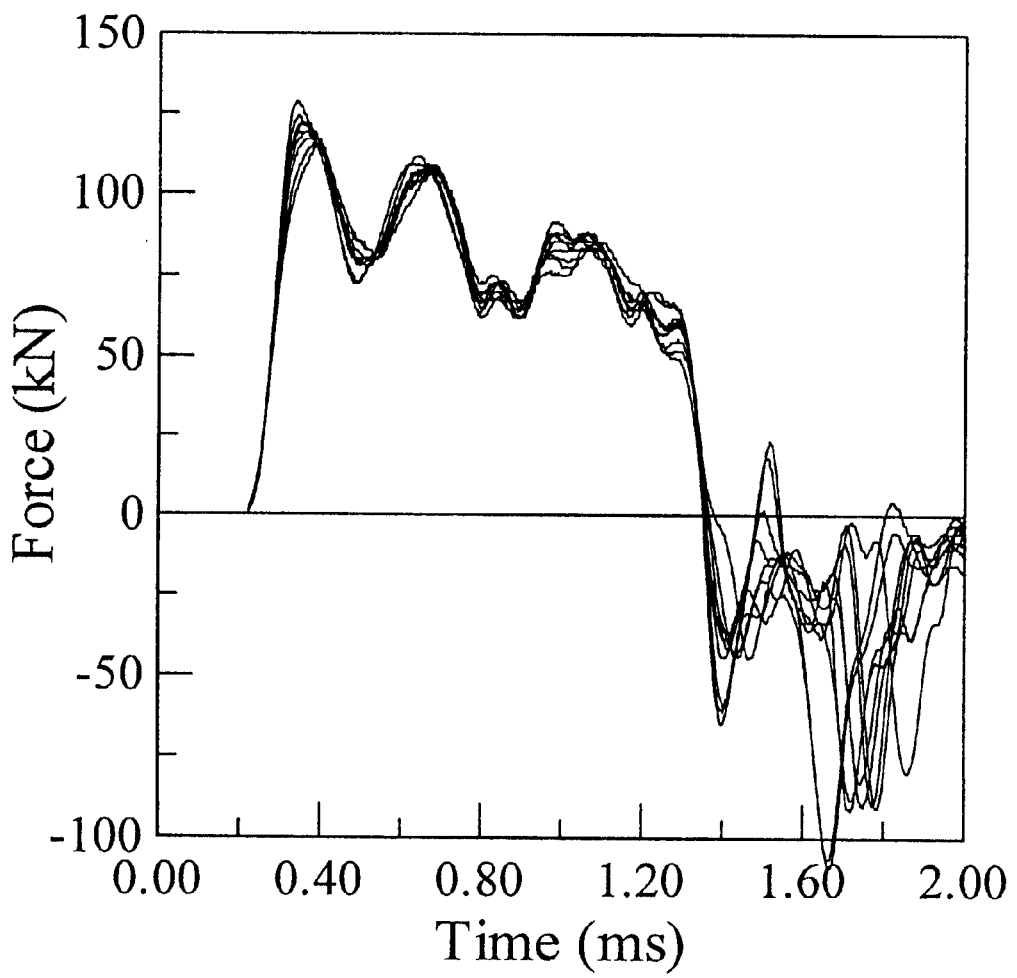
FIGS. 6(*a*) to (*d*) are graphs of the measured force-time histories of the experiments using a round-top anvil in accordance with the present invention and various hammers.
Figure 6B:
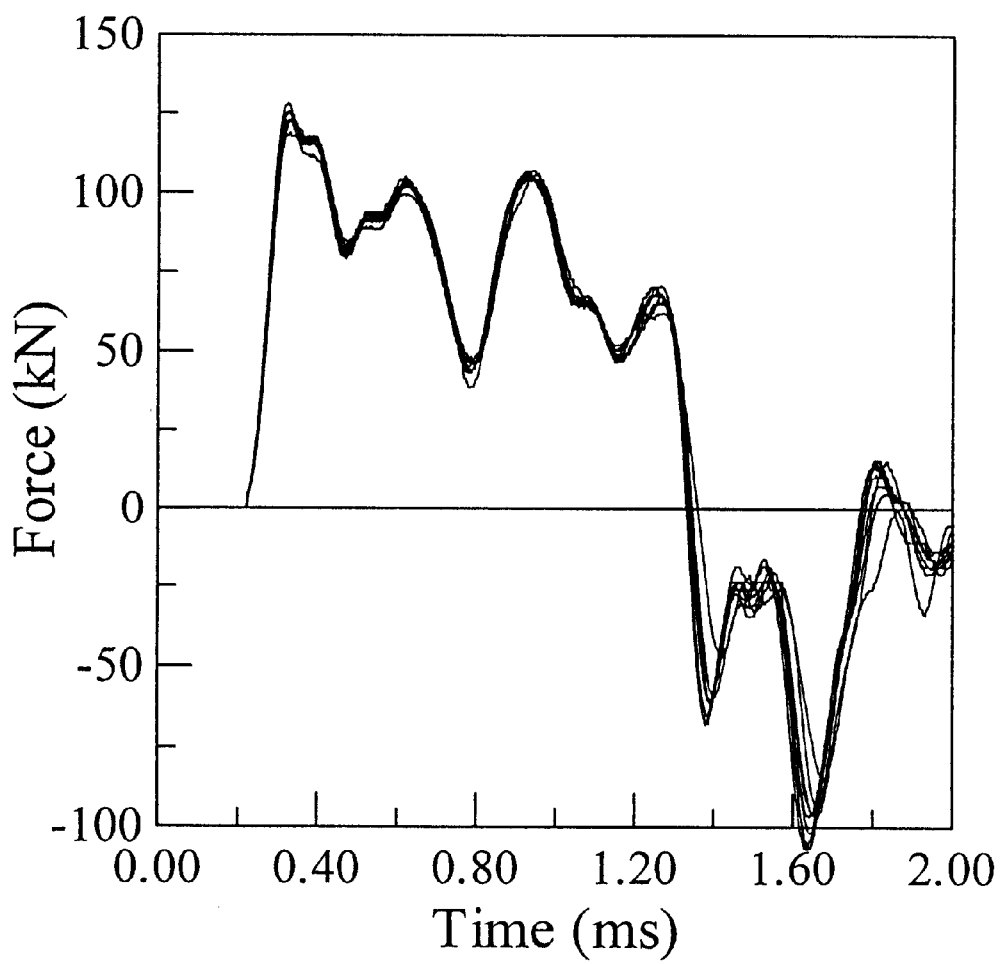
Figure 6C:
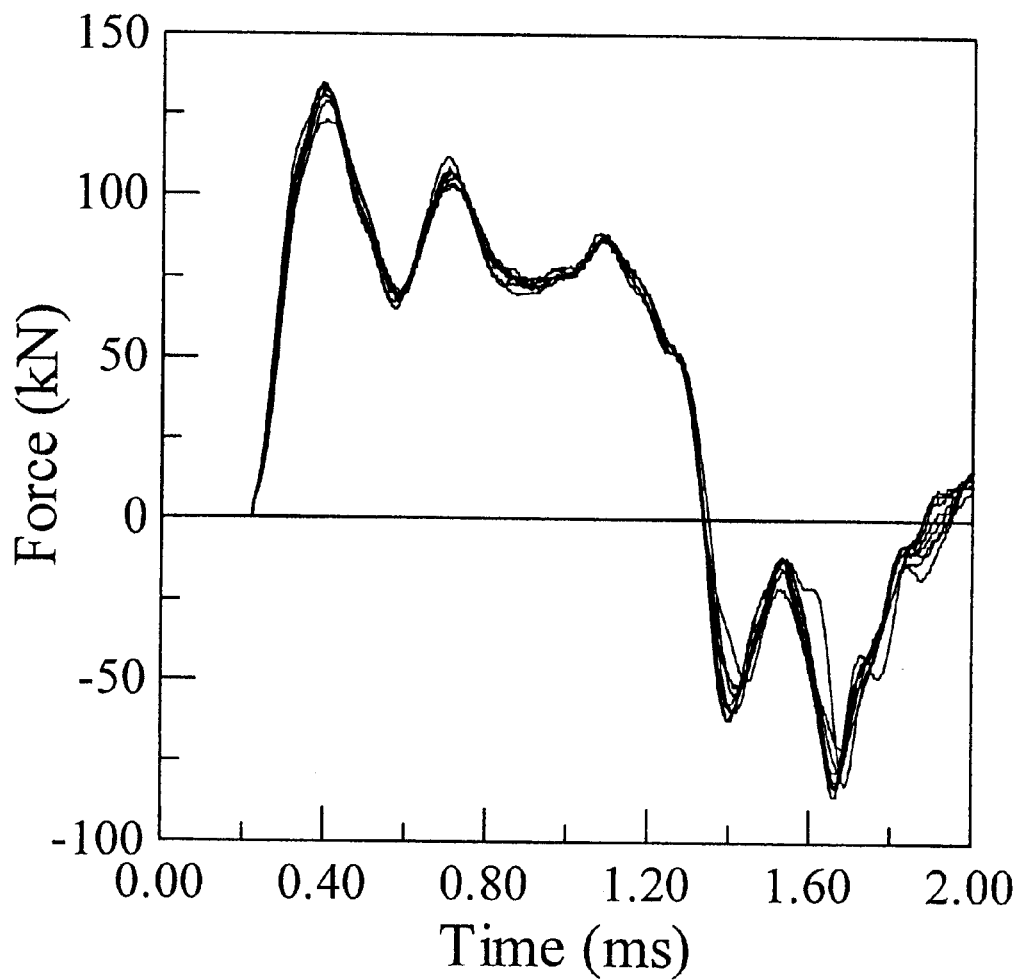
Figure 6D:
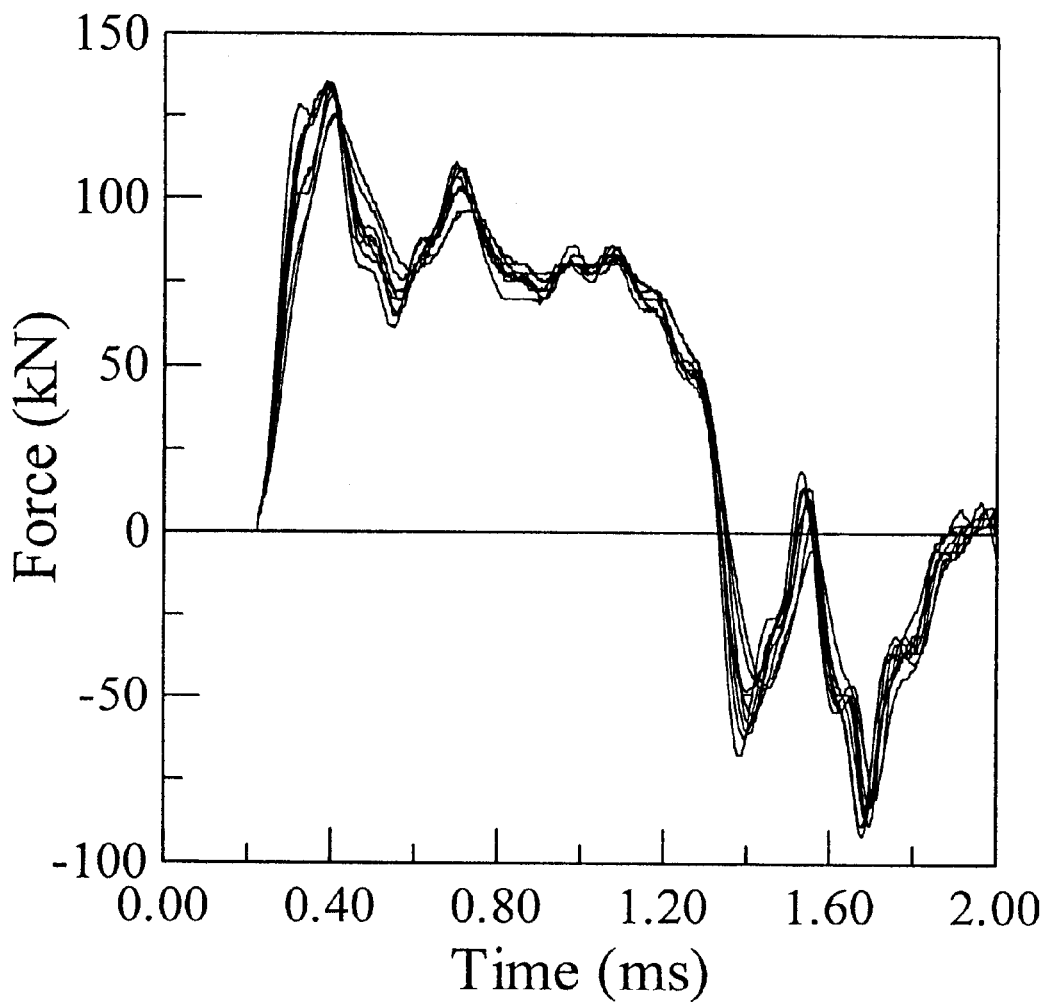
Figure 7A:
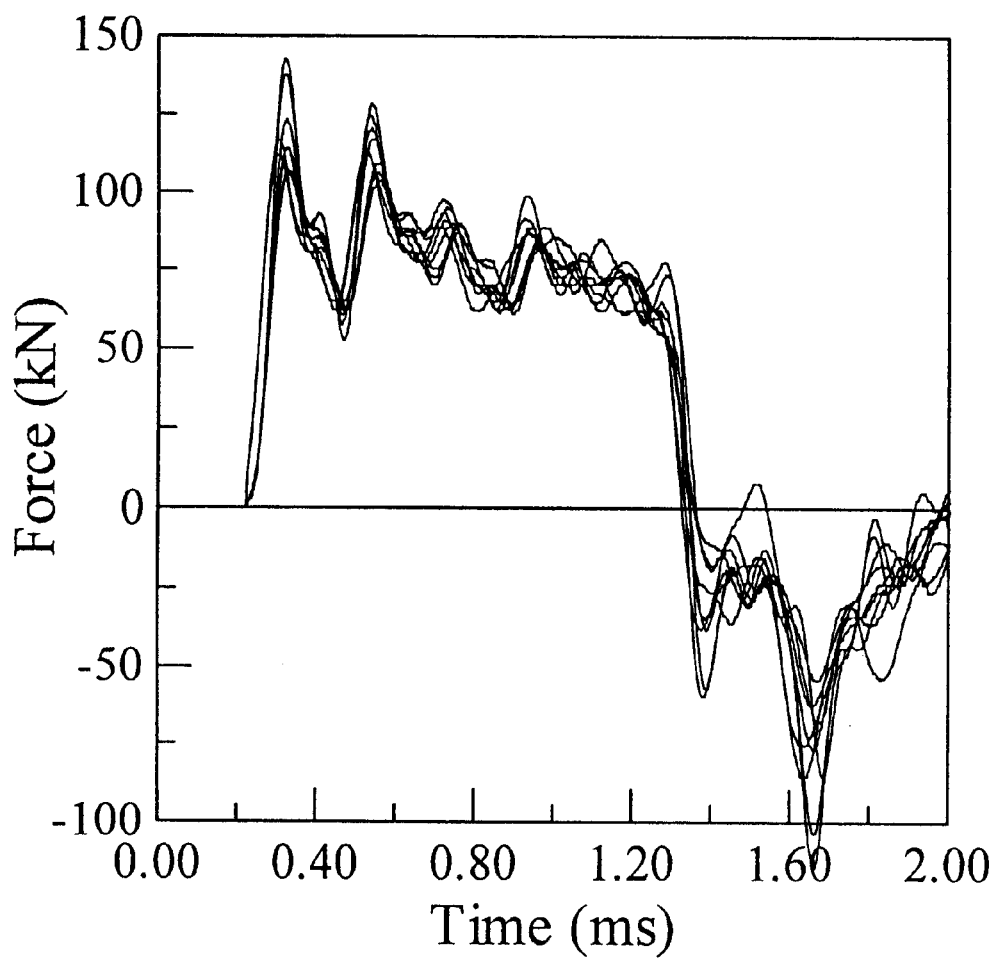
FIGS. 7 (*a*) to (*d*) are graphs of the measured force-time histories of the experiments using a flat top anvil and various hammers.
Figure 7B:
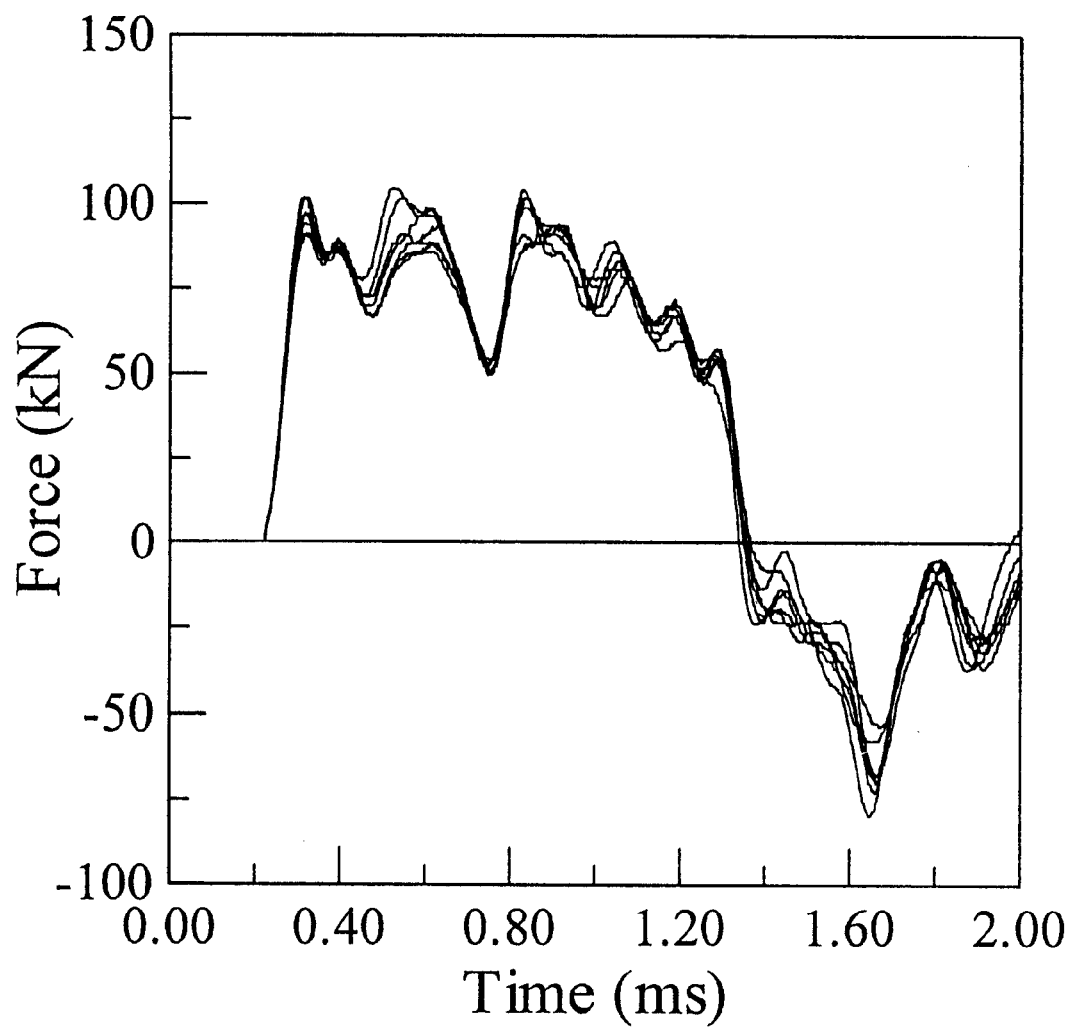
Figure 7C:
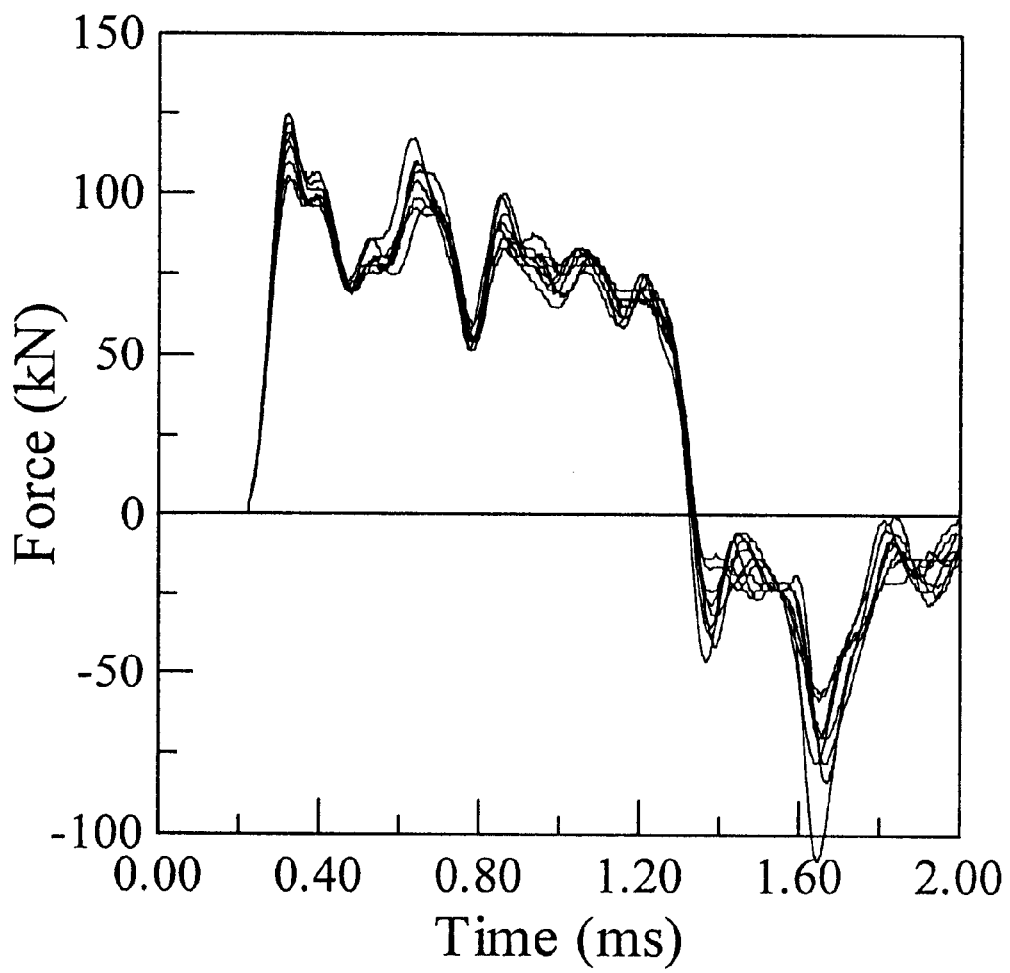
Figure 7D:
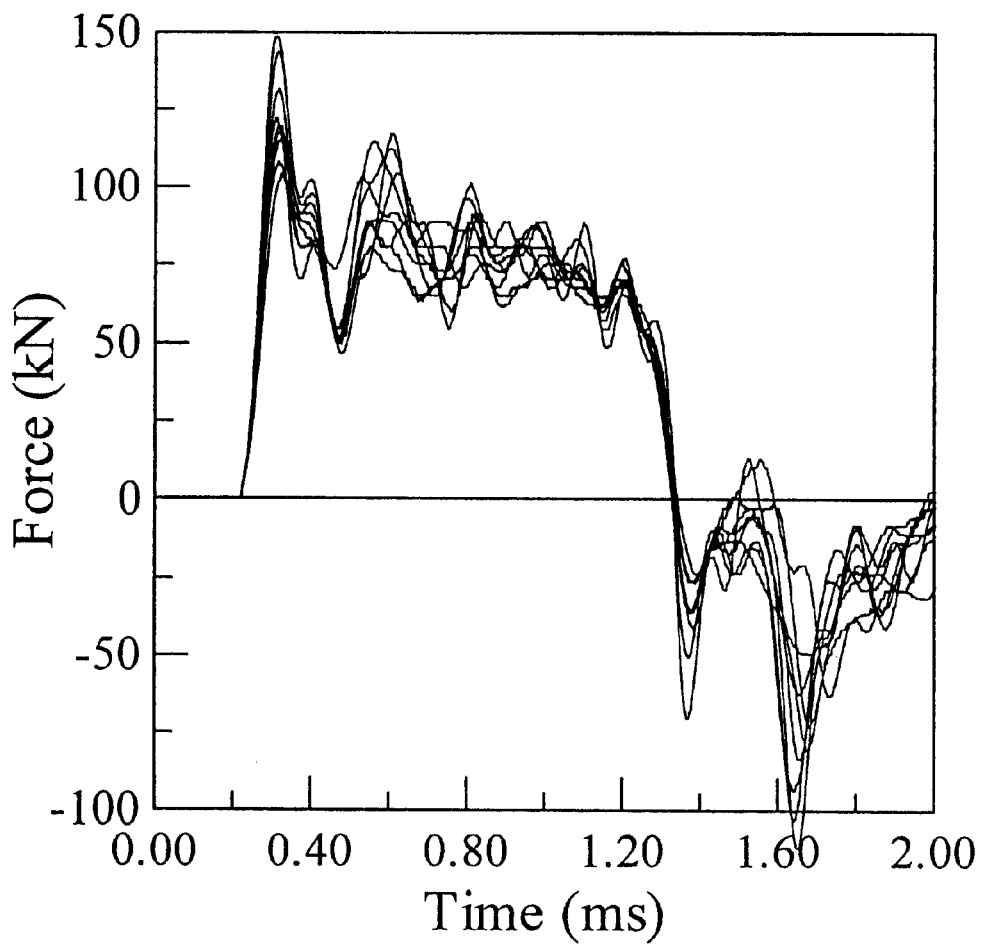
Figure 8:
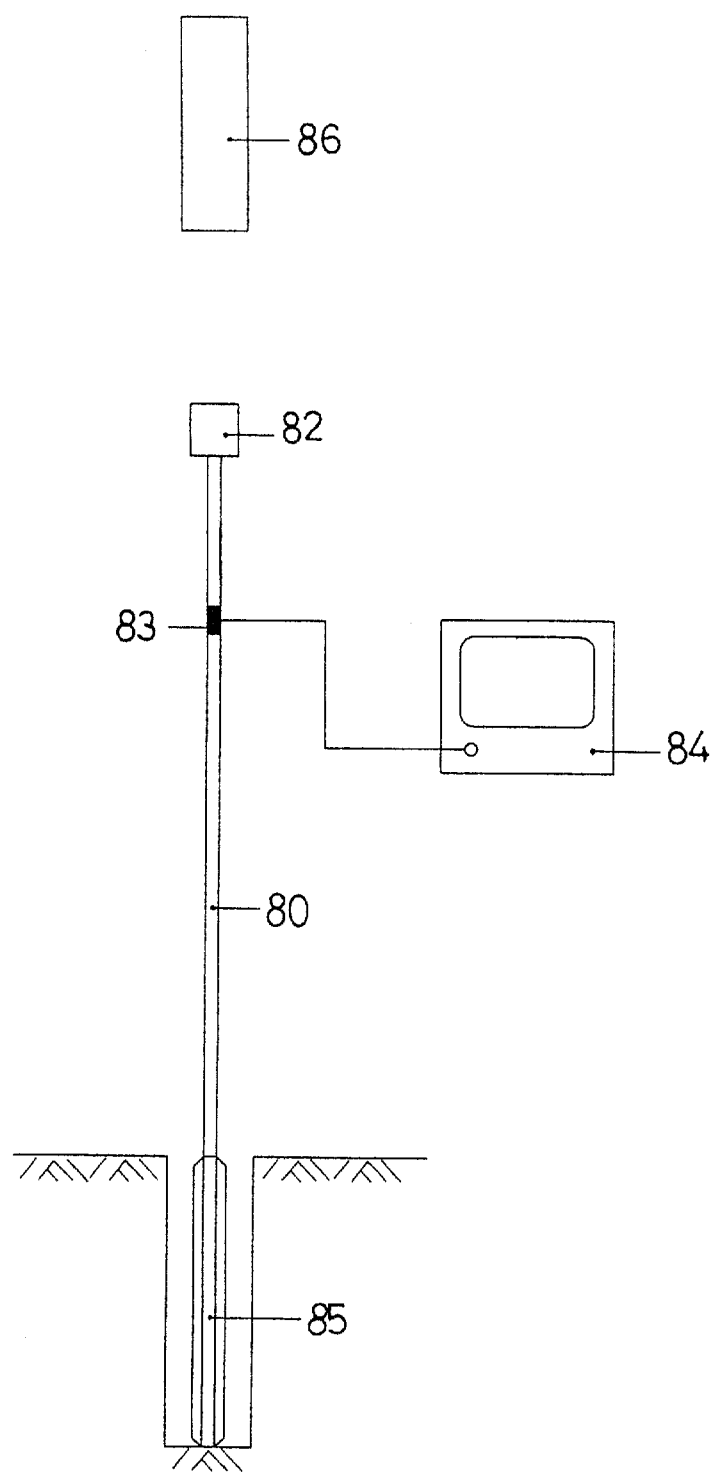
FIG. 8 is the fundamental equipment setup for the conventional SPT.

In order to prove the shape of the anvil does affect the energy transfer in the SPT, experimental tests were conducted using both round top and flat top anvils. Hammers of four different configurations as described in FIG. 3, including a safety hammer and three cylindrical hammers, were employed in the tests to examine the anvil effect. FIGS. 4 and 5 show the test results, in which both the efficiency and the consistency of the SPT energy transfer were remarkably improved when the flat top anvil was replaced by the round top anvil. Two important factors are examined in the experiments; one is the total energy transmitted and the other is the consistency of energy transmission between different hammer strikes. From the total energy transmitted perspective, the present experiments show that the average energy transfer ratio (ERr) increases from 51% of the flat top anvil cases to 59% of the round top anvil cases, which is about 8% improvement (FIG. 5). The present experiments were carried out by using a three meter rod (11). In common practice, the impact energy is described assuming an infinitely long rod. Therefore, the above described energy transfer ratios (ERr) have to be corrected as the corrected energy transfer ratio (ERi) according to the standard procedure specified in ASTM 4633-86. After correction, the average ERi for the flat top anvil cases is 88% and the ERi for the round top anvil cases is 100%. Note that ERi=100% means no energy loss in the SPT experiment. This also means that there is almost no energy lost when a round top anvil is employed. One should conclude from the results of these experiments that the round top anvil greatly improves the impact energy transmission characteristics over the currently used flat top anvil in the SPT.

From the perspective of the consistency of energy transmission, the total range of variation in the data for the flat top anvil cases is about 18% (the variation is about ±9%), and the total range of variation for the round top anvil cases is about 4% (the variation is about ±2%). The improvement in the consistency of energy transmission is about 14%. With reference to FIG. 6, the force-time histories measured during hammer impacts were nearly repeatable. Since the energy transfer ratio is calculated by direct integration of the force-time history, the repeatability of the force-time history indicates the consistency of the energy transmission of the round top anvil cases. From FIGS. 6(a) to (d), all cases of the hammers in different shapes show the same phenomena. On the other hand, with reference to FIGS. 7(a) to (d), again with different hammers, the measured force-time histories for the flat top anvil cases indicate poor repeatability, which shows that the errors generated in the flat top anvil cases are much greater.

Based on the experimental proof, it can be concluded that the amount of impact energy transmitted to the rod from the hammer greatly increases if the point contact impact is generated by using the round top anvil, disregarding the shape and the type of the hammer. Also, the consistency of energy transmission increases simply because the impact takes place at or very near the center of the anvil, which minimizes the most likely error during the impact. With the present invention, the efficiency of the impact energy transfer and the accuracy of the SPT results can be considerably improved. As a result, future SPT equipped with the device in accordance with the present invention can serve as a better indicator to describe the subsurface soil profile, and engineers will have better data to understand the soil's capacity to resist ground failure or excessive settlement. Even though numerous characteristics and advantages of the present invention have been set forth in the foregoing description, together with details of the structure and the function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A point-contact impact method used in the Standard Penetration Test (SPT), the method comprising the steps of:

free falling a drop hammer to an anvil having an anvil face;

forming the impact between the hammer and the anvil in the form of point contact; and centering the impact contact on the anvil face.

2. The method as claimed in claim 1, wherein the impact centering step uses a rounded anvil face and a flat hammer face.

3. The method as claimed in claim 1, wherein the impact centering step uses a flat anvil face with a small bump at the center of the anvil face and a flat hammer face.

4. The method as claimed in claim 1, wherein the impact centering step uses a curved anvil face with a small bump at the center of the anvil face and a flat hammer face.

5. The method as claimed in claim 1, wherein the impact centering step uses a curved anvil face and a curved hammer face.

6. A device used in the Standard Penetration Test, wherein the device comprises:

a rod with a split-barrel sampler in contact with the ground attached to one free end;

an anvil securely mounted on the other free end of the rod; and a drop hammer repeatedly striking a face of the anvil after freefalling;

wherein the anvil face struck by the drop hammer is shaped to generate a point contact condition.

7. The device as claimed in claim 6, wherein the contact face of the anvil is rounded.

8. The device as claimed in claim 6, wherein the contact face of the anvil is curved.

9. The device as claimed in claim 6, wherein the contact face of the anvil is flat with a bump at the center of the anvil face.

10. The device as claimed in claim 6, wherein the contact face of the anvil is curved with a bump at the center of anvil face.

11. The device as claimed in claim 6, wherein the contact face of the drop hammer is flat.

12. The device as claimed in claim 6, wherein the contact face of the drop hammer is rounded.

13. The device as claimed in claim 6, wherein the contact face of the drop hammer is curved.

* * * * *